United States Patent [19]
Glassman

[11] Patent Number: 4,805,605
[45] Date of Patent: Feb. 21, 1989

[54] ABDUCTION PILLOW

[75] Inventor: Andrew H. Glassman, Alexandria, Va.

[73] Assignee: Glassman Medical Products, Inc., Columbus, Ohio

[21] Appl. No.: 142,177

[22] Filed: Jan. 11, 1988

[51] Int. Cl.⁴ .............................................. A61F 5/00
[52] U.S. Cl. .................................... 128/80 A; 5/443; 128/882
[58] Field of Search ............... 128/76 R, 80 R, 80 A, 128/87 C, 133; 5/424, 437, 443, 444

[56] References Cited
U.S. PATENT DOCUMENTS

| | | | |
|---|---|---|---|
| 3,828,377 | 8/1974 | Eary, Sr. | 128/76 R X |
| 4,327,714 | 5/1982 | Spann | 128/80 A |
| 4,372,299 | 2/1983 | Fixel | 128/80 A |
| 4,392,489 | 7/1983 | Wagner, Sr. | 128/80 A |

Primary Examiner—Edgar S. Burr
Assistant Examiner—Moshe I. Cohen
Attorney, Agent, or Firm—Biebel, French & Nauman

[57] ABSTRACT

An abduction pillow to prevent early hip dislocation following hip arthroplasty or endoprosthetic hemiarthroplasty without attendant problems of heel pressure sores, stretch injuries to soft tissues and difficulties with elimination and perineal care is provided by forming the abduction pillow with two principal sections mounted on a base pad to which a patient's lower extremities can be secured by means of strap with a cephalad rhomboid-shaped section positioned upwardly between the patient's thighs and a lower, similarly shaped, but larger caudad section position between lower portions of the patients legs and with the patient's heels elevated, free from pressure with the base pad. With the main body portion of the pillow formed as separate sections, their line of demarcation can be positioned approximately at the patient's knees and above the break point of a conventional hospital bed to permit flexion of the patient's lower extremities and reduced tension on associated soft tissues.

10 Claims, 2 Drawing Sheets

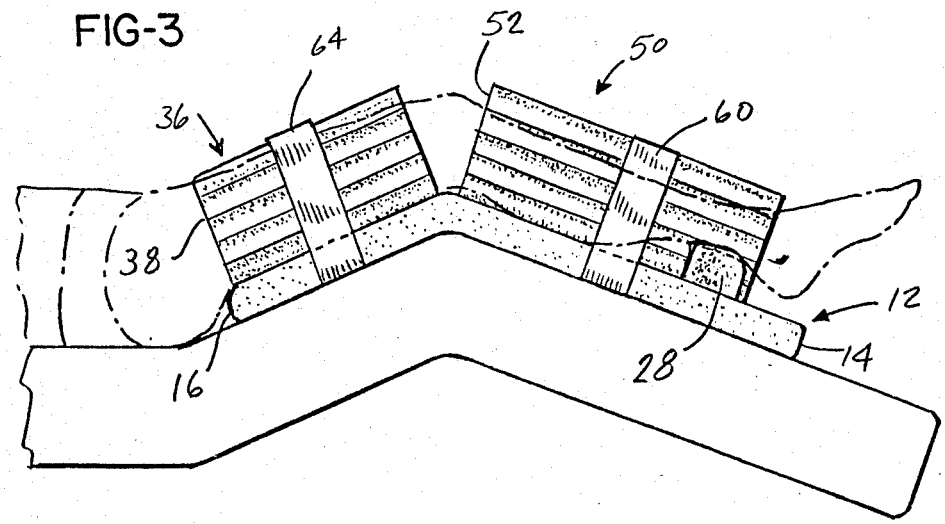
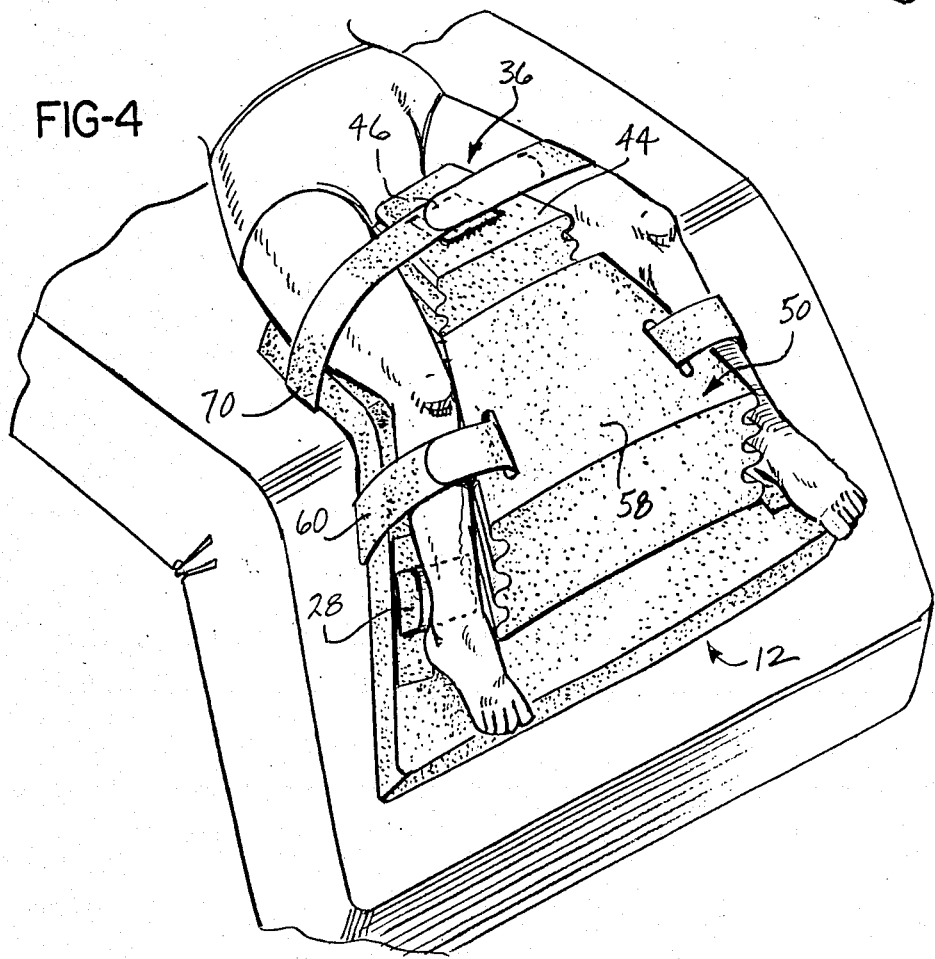

ABDUCTION PILLOW

BACKGROUND OF THE INVENTION

The postoperative management of patients having undergone total hip arthroplasty or endoprosthetic hemiarthroplasty usually includes measures to prevent early dislocation. Adduction especially increases the risk of dislocation and hence pillows or splints which maintain the hip in an abducted position are commonly employed. Such devices are commercially available from a variety of manufacturers. Despite variations in base material, usually some form of foam rubber, and covering, e.g. cloth, vinyl, most pillows have basically the same design. This includes a triangular or rhomboid shape such that the apex fits between the thighs proximally and the broader base fits between the ankles, thereby maintaining the desired abduction. Retention straps attached to the pillow secure it in place by encircling the legs above and below each knee.

This design has proven quite effective in maintaining the desired position of abduction. However, several problems have been associated with its use, ranging in magnitude from minor inconveniences to major complications with potentially permanent impairment of function. These include pressure sores of the heels, stretch injuries to soft tissues, and difficulties with elimination and perineal care.

With respect to the first of these it will be noted that current designs of abduction pillows utilize retention straps above and below the knees. Because the pillow itself is generally fairly rigid, it acts as a splint to maintain the knee in full extension. With the leg cinched against the pillow, a situation can arise in which the buttock proximally and the heel distally are the only firm points of contact between the leg and the bed. The heel then supports a large portion of the weight of the leg, distributing it over the very small surface area of the heel.

This is aggravated by the fact that in the immediate post operative state, the patient is usually heavily sedated, and often is given high doses of narcotic analgesics. Normal protective sensation can be markedly impaired by these medications. The situation is even more dramatic for the patient in whom spinal or epidural anesthesia has been used, in that they may have no protective sensation to the lower extremities for hours.

Combined with the immobility imposed by the abduction pillow and sedating medications, the stage is set for pressure injury to the backs of the patient's heels. Only a few hours of excessive pressure to skin with compromised protective sensation is sufficient to initiate tissue damage. Degrees of injury are similar to those applied in describing burns. In the mildest form, this amounts to reddening and an uncomfortable burning sensation for the patient. Next in severity is blistering of the skin. This usually eventuates in a sizable vesicle which then breaks and is quite painful. In the most severe form of injury there can be full thickness skin loss and eschar formation necessitating debridement and later skin grafting.

As indicated, stretch injuries to soft tissues comprises another potential problem associated with conventional abduction pillow use. Thus, as a result of the disease process underlying the necessity for total hip replacement, there is often shortening of the involved extemity as a result of loss of the joint space, collapse of the femoral head, protrusion of the femoral head centrally through the acetabulum or subluxation of the hip. Whatever the mechanism, the shortening can amount to several centimeters in severe cases. Along with these changes in the bones, there are parallel changes in the soft tissue envelope surrounding the hip joint such that secondary shortening of the muscles, nerves, blood vessels and fascial sleeves takes place.

At the time of surgery, a major objective is the restoration of normal leg length. Whereas this can be accomplished within the time span of the operation, the soft tissue changes described above, which probably developed over a period of years, require several weeks to stretch out and accommodate the new leg length. Several muscles, particularly those in the hamstrings group, cross both the hip and knee joints, and have maximal tension placed upon them when the knee joint is obligated to a position of full extension. Such is the case with current designs of abduction pillows.

This tension on major muscle groups and fascial sleeves can result in severe muscle spasm and pain for the patient. The major neurovascular structures of the lower extremity are subjected to the same stretching phenomena. Patients in whom neurovascular status of the lower extremity was completely intact on the evening of a surgery in which the leg was lengthened, may be found to have incurred a peroneal palsy the following morning after immobilization in an abduction pillow over night with the knee in full extension. Damage to this division of the sciatic nerve can be permanent. In similar fashion, vascular compromise of the lower extremity can result from leg lengthening followed by post operative immobilization with the knee in extension. This is particularly so in the patient with significant atherosclerotic peripheral vascular disease.

Lastly, current abduction pillow design inevitably results in difficulties with elimination and perineal care. These arise from the fact that conventional abduction pillows fit quite high between the thighs, such that in order to use a bedpan or a urinal, it is necessary to remove the retention straps and either completely remove the pillow or to slide it distally a significant distance. The same holds true for the performance of routine perineal care.

SUMMARY OF THE INVENTION

The abduction pillow of the present invention avoids the problems associated with conventional abduction pillows noted above while effectively maintaining a position of abduction and thereby reducing the chances of early postoperative dislocation.

Thus, an abduction pillow in accordance with the present invention includes four principal components: a body, a base pad, ankle rests and retention straps; each of which both satisfies a particular requirement of the improved design and also cooperates with the remaining components to reduce the likelihood of postoperative dislocation while obviating the serious disadvantages of conventional designs noted supra.

The body of the abduction pillow is similar in shape to a conventional abduction pillow in that it is generally rhomboid in configuration and may be fashioned of medium density foam rubber. However, in contrast to conventional designs it is formed as two smaller, rhomboid-shaped sections, one cephalad and one caudad relative to the supine patient. The line of division between the two corresponds to a line connecting the axes of rotation of the knee joint lines in the coronal plane, a detail whose significance will shortly become apparent.

The base pad is also of rhomboidal shape, larger in area than the pillow body, but congruent to it and preferably composed of a high density foam rubber. The base pad not only provides the primary support for the patient's limbs, but also serves as the basic component to which all of the other components are attached and thus located relative to each other to achieve the desired total effect described above.

The ankle rests are also preferably formed of a relatively high density foam rubber and have a concave upper surface and a flat base covered with a hooked nylon fastener of the type sold under the trademark VELCRO, and adaped to engage with foam backed fabric strips on the base pad. The ankle rests can therefore be secured anywhere from proximal to distal along these fabric strips and hence, their position is adjustable. The foam backed fabric strips provide for quite secure fixation of the ankle rests, yet are smooth and soft to the touch.

The fourth major feature of the invention is the set of retention straps. They include proximal and distal straps for both the left and right limbs of the patient, and are attached to and cooperate with the other components in the manner described below.

BRIEF DESCRIPTION OF THE DRAWINGS

FIG. 3 is a side elevational view showing a patient's legs secured to the abduction pillow of the present invention; and FIG. 4 is a perspective view illustrating the positioning of components relative to each other and the patient's extremities.

DESCRIPTION OF THE PREFERRED EMBODIMENTS

Figure 1:
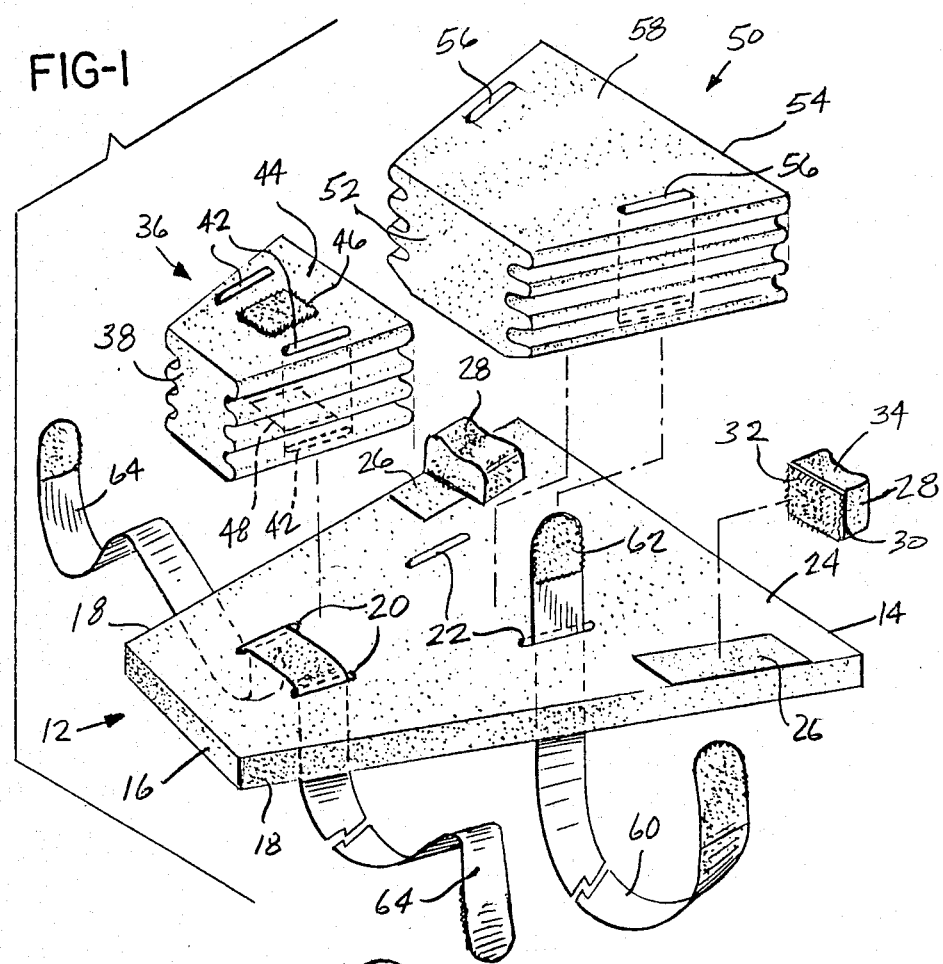
FIG. 1 is an exploded perspective view of the abduction pillow of the present invention in accordance with a first preferred embodiment thereof.

With reference initially to FIG. 1 of the drawings, it will be seen that an abduction pillow 10 in accordance with the present invention includes a base pad 12 of generally rhomboid shape, including major and minor edges 14 and 16, respectively, and diverging side edges 18. A cephalad portion is provided with a pair of slots 20, while a caudal portion is provided with a pair of slots 22, both pairs of slots extending completely through the base pad. Additionally, the upper surface 24 of the base pad is provided with a pair of fabric strips 26 having a surface adapted to be engaged by hook-like material of the type sold under the trademark VELCRO. Ankle rests 28, each having a flat base 30 covered with a hook-like material 32 and a concave upper surface 34 are adapted to be attached to the fabric strips 26.

A cephalad section 36 of generally rhomboid shape, including minor and major bases 38 and 40, respectively, has a pair of slots 42 extending completely through it from its upper surface 44 to a lower surface thereof, and the upper and lower surfaces are provided with pads of hook-like material 46 and 48, permanently secured thereto by adhesive or the like.

A caudad section 50 also has minor and major bases 52 and 54 and slots 56 extending completely through the section from an upper surface 58 to a lower surface thereof.

The caudad section 50 is permanently secured to the base pad 12 by adhesive or the like with the slots 56 and 22 aligned so that pairs of straps 60 may extend through the aligned slots 22 and 56. Each of the straps 60 is preferably constructed of a foam backed fabric adapted to be engaged by pads 62 of a hook-like material.

In one preferred embodiment of the invention a similar, foam-backed fabric strap 64 of substantially greater length than the straps 60 is threaded downwardly through the slots 20, as seen in FIG. 1 of the drawings, with the central portion of the strap 64 extending between the slots 20 engaged by the lower pad 48 of hook-like type material of the cephalad section 36.

Figure 2:
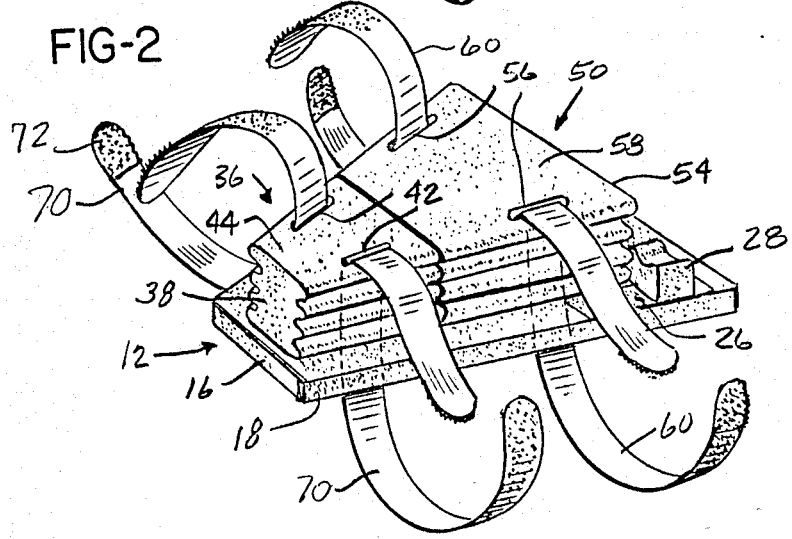
FIG. 2 is a view similar to FIG. 1 of a second preferred embodiment of the invention.

Alternatively, and as seen in FIG. 2 of the drawings, a pair of shorter, foam-backed fabric straps 70 may be employed at the cephalad section of the abduction pillow, each strap passing through aligned slots 42 and 20 in the cephalad section 36 and base pad 12, respectively, with each strap 70 having a pad 72 of hook-like material for engagement with the strap, similarly to straps 60.

With the above constructions the abduction pillow is positioned such that the minor base 38 of the cephalad section 36 is positioned close to but not against the genitals of the patient, with the lower extremities of the patient extending along opposite sides of the cephalad and caudad sections and resting on those portions of the base pad extending outwardly from the sides of the sections. The upper or minor base 52 of the caudad section and the lower or major base 40 of the cephalad section are positioned such that they occur at the joint axes of the knees of the patient or slightly below and above, respectively.

Strap 64 of the embodiment of FIG. 1 is then secured snugly about the thighs of the patient by passing its outer ends beneath the base pad, outwardly around its side edges 18 and up to the upper surface 44 for engagement with the pad 46.

Alternatively, and with respect to the embodiment of FIG. 2, each of the straps 70 are secured about the patient's thighs and attached to themselves by means of the pads 72.

Straps 60 are secured in a manner similar to the straps 70, passing outwardly around the side edges 18 of the base pad 12 and secured upon themselves by the fastener pads 62.

The ankle rests 28 are positioned just cephalad to the heels of the patient such that their concave surfaces 34 conform to the convex shape of the patient's ankles at the level of the Achilles' tendon.

With the above construction it will be seen that the high density foam of the base pad 12 forms a cushion to support the entire lower extremity of the patient and results in a more even distribution of pressure along the patients limbs. In addition, the ankle rests elevate the entire foot above the surface of the bed such that there is no contact between the heels and the mattress. Heel sores are thereby averted.

As noted previously, a major contributing factor to stretch injuries to soft tissues with rigid, conventional abduction pillows is the obligatory position of full knee extension when the pillow is strapped into place above and below the knee. With the abduction pillow of the present invention the taut soft tissues are "unloaded" by the introduction of gentle hip and knee flexion made possible by virtue of the formation of the pillow body into separate cephalad and caudad segments.

Ideally, the transverse split between the cephalad and caudad sections is positioned over the break used for knee elevation in conventional electric hospital beds. When the bed is "broken" and elevated at this point, the abduction pillow of the present invention hinges open anteriorly and the knees flex comfortably. There is no loss of hip abduction, and the straps 60 and 64, 70 remain secure without binding. Soft tissues are relaxed and the risk of their incurring significant injury is considerably reduced.

As previously noted, perineal hygiene and bedpan and urinal use are greatly simplified if they can be accomplished without the need for removing the entire abduction pillow. With the present invention it is only necessary to remove only the strap 64 or the pairs of straps 70 and the entire cephalad section of the abduction pillow can be removed and replaced after the patient's needs have been attended to without change in leg position.

It will be seen, therefore, that the present invention provides an improved abduction pillow which secures a patient's lower extremities in an abducted position to prevent dislocation following hip arthroplasty or endoprosthetic hemiarthroplasty while obviating the serious disadvantages of conventional abduction pillows and post operative splints.

While the products herein described constitute preferred embodiments of the invention, it is to be understood that the invention is not limited to these precise products, and that changes may be made therein without departing from the scope of the invention which is defined in the appended claims.

What is claimed is:

1. An abduction pillow comprising:
   a base pad of a shape and sufficient size to accommodate a patient's lower extremities in an abducted position,
   a cephalad section secured to an upper surface of said base pad proximally thereof and received between the thighs of a patient's lower extremities in an abducted position with a lower edge of said cephalad section terminating at a point at or above the knees of said patient,
   a caudad section separate from said cephalad section and secured to said outer surface of said base pad distally thereof and received between said patient's lower extremities with an upper edge of said caudad section terminating at a point at or below the knees of said patient, and
   means for securing said patient's lower extremities to said base pad with said cephalad section extending from said point at or above said patient's knees toward said patient's genitals and said caudad section extending from said point at or below said patient's knees toward said patient's ankles, whereby said patient's lower extremities may be flexed at said knees and soft tissues thereof unloaded.

2. The abduction pillow of claim 1 wherein said cephalad section is removably secured to said upper surface of said base pad.

3. The abduction pillow of claim 1 further comprising heel elevating means removably secured to said base pad and positionable at varying positions therealong.

4. The abduction pillow of claim 1 wherein said securing means comprise straps adapted to extend about the lower extremities of said patient.

5. The abduction pillow of claim 1 wherein said base pad, cephalad and caudad sections are substantially rhomboidal in shape.

6. The abduction pillow of claim 1 further comprising aligned slots extending through said base pad and said caudad section, and said securing means comprises straps extending through said aligned slots.

7. The abduction pillow of claim 1 wherein said caudad section is permanently attached to said base pad.

8. The abduction pillow of claim 1 wherein said base pad is provided with a pair of slots extending therethrough beneath said cephalad section, and said securing means comprises a strap extending downwardly through said slots.

9. The abduction pillow of claim 1 further comprising aligned pairs of slots formed through said cephalad section and said base pad, and said securing means comprises straps extending through said aligned slots.

10. An abduction pillow comprising:
    a substantially rhomboid shaped base pad formed of a high density foam rubber and having major and minor bases and interconnecting side edges,
    means defining a first pair of slots through said base portion adjacent said minor base thereof and inwardly of said side edges and a second pair of slots adjacent said major base thereof and inwardly of said side edges,
    a cephalad section of substantially rhomboid shape having major and minor bases and interconnecting side edges removably secured to said base pad with said major and minor bases and side edges thereof substantially parallel to but disposed inwardly of said major and minor bases and side edges of said base pad,
    a caudad section of substantially rhomboid shape having major and minor bases and interconnecting side edges permanently affixed to said base pad with said major and minor bases and side edges of said caudad section disposed parallel to but inwardly of said major and minor bases and side edges of said base pad,
    fabric strips positioned along an upper surface of said base pad outwardly of said side edges of said caudad section,
    heel rests having substantially flat bases covered by a hook-type fastener material and concave upper surfaces removably secured to said fabric strips by means of said hook-type fasteners,
    means defining aligned pairs of slots through said caudad section and underlying portions of said base pad,
    straps extending through said aligned slots in said caudad section and said base pad for securing a patient's lower extemities to said abduction pillow,
    means defining a pair of slots through said base pad beneath said cephalad section, and
    strap means extending through said slots beneath said cephalad section for securing a patient's lower extemities to said abduction pillow said cephalad section extending from a point at or above said patient's knees toward said patient's genitals and said caudad section extending from a point at or below said patient's knees toward said patient's ankles, whereby said patient's lower extremities may be flexed at said knees and soft tissues thereof unloaded.

* * * * *